United States Patent [19]
Crawford et al.

[11] 4,175,436
[45] Nov. 27, 1979

[54] WET/DRY BULB HYGROMETER WITH AUTOMATIC WICK FEED

[75] Inventors: William B. Crawford, Greensboro; Vernon T. Daniel, Oak Ridge; Kenneth Y. Wang, Greensboro, all of N.C.

[73] Assignee: Burlington Industries, Inc., Greensboro, N.C.

[21] Appl. No.: 937,199

[22] Filed: Aug. 28, 1978

[51] Int. Cl.[2] ............................................. G01N 25/62
[52] U.S. Cl. .................................................... 73/338.6
[58] Field of Search ............... 73/338, 338.3, 338.6; 236/44 C

[56] References Cited

U.S. PATENT DOCUMENTS

| | | | |
|---|---|---|---|
| 1,601,243 | 9/1926 | Irwin, Jr. | 73/338.6 |
| 1,636,350 | 7/1927 | Armstrong | 73/338.6 |
| 2,688,252 | 9/1954 | King, Jr. | 73/338.6 |
| 3,303,700 | 2/1967 | Kahl | 73/338.6 |
| 3,459,034 | 8/1969 | Kawaguchi | 73/338.6 |
| 3,869,529 | 3/1975 | Follette | 236/44 C X |
| 3,890,828 | 6/1975 | Pleva | 73/338.6 X |

*Primary Examiner*—John Petrakes
*Attorney, Agent, or Firm*—Cushman, Darby & Cushman

[57] ABSTRACT

A wet/dry bulb hygrometer of the psychrometer type is used for monitoring and/or controlling humidity of a gaseous fluid having contaminants therein. The wet bulb sensor of the hygrometer is provided with a wick which is movable over the wet bulb sensor so that a fresh wicking surface is presented to the gas stream and contaminants will not render the sensor useless for accurate measurements. The hygrometer is used to monitor and/or control humidity and temperature in a textile processing environment wherein lint, fumes, condensable oils, tints and resins would tend to foul a stationary wick of a web bulb sensor and, consequently, a wick material is moved into and through the hygrometer over the wet bulb sensor and then out of the hygrometer, thus, always presenting a fresh wicking surface for the gaseous fluid stream.

24 Claims, 10 Drawing Figures

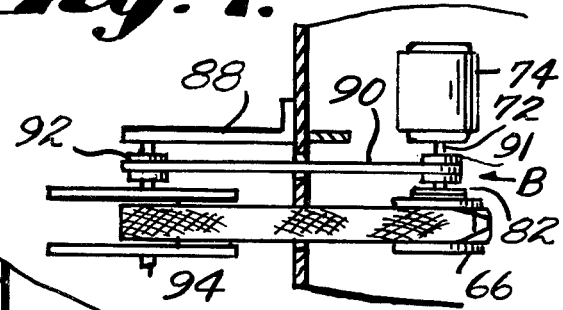
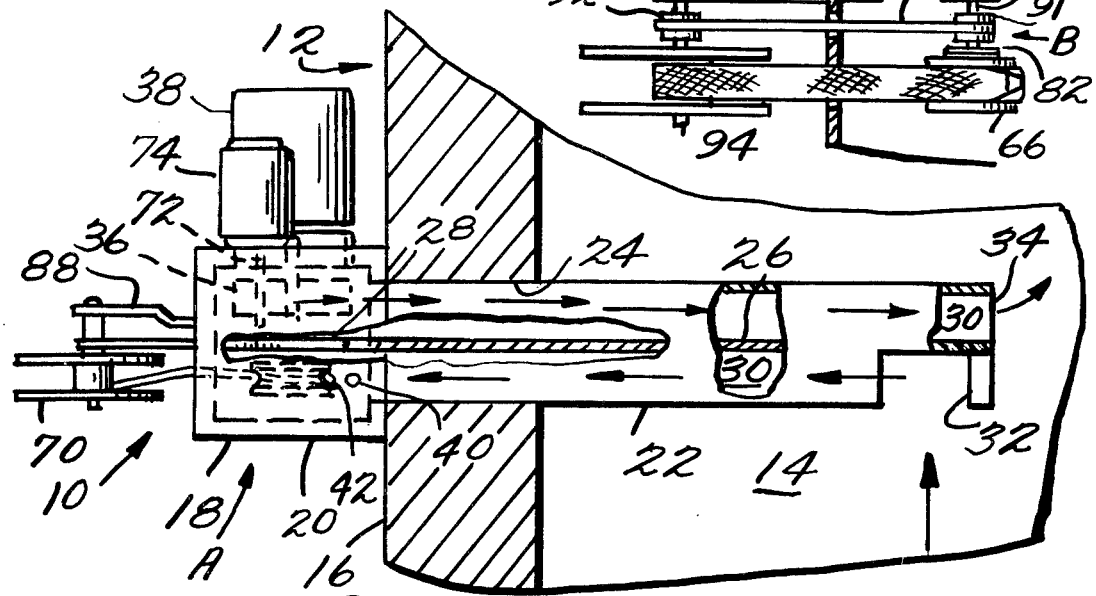
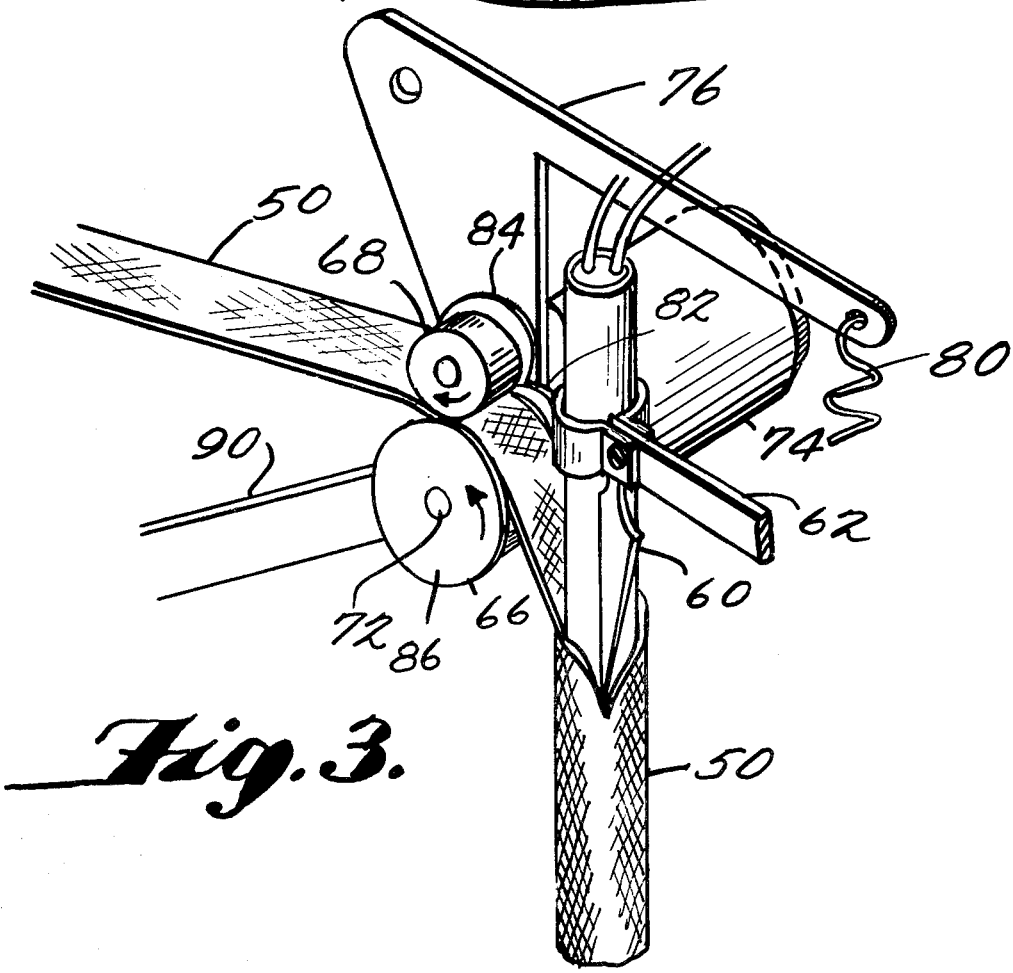

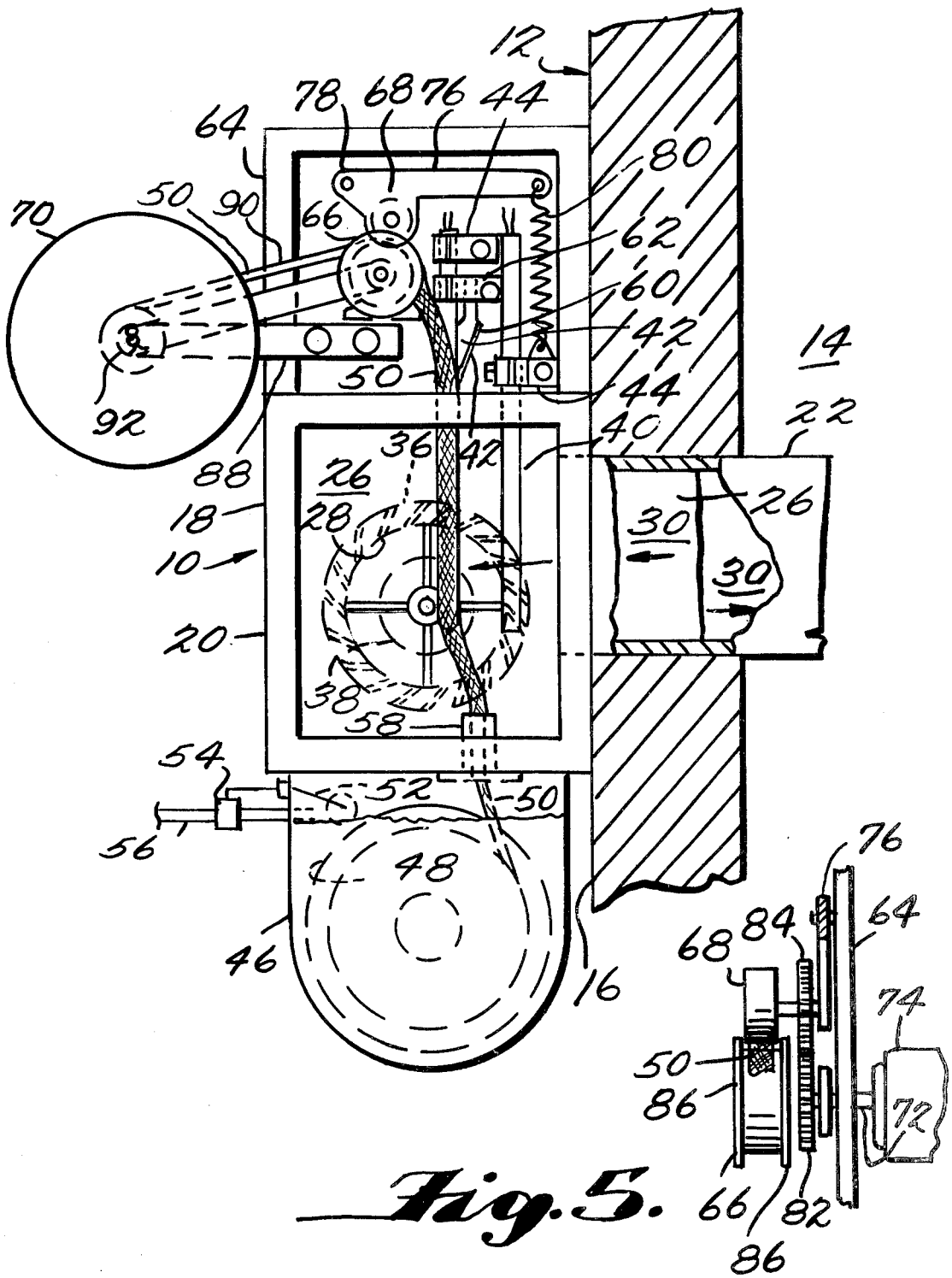

WET/DRY BULB HYGROMETER WITH AUTOMATIC WICK FEED

The present invention relates to a wet/dry bulb hygrometer, sometimes referred to as a psychrometer, the device being used for monitoring and/or controlling humidity and temperature of a gaseous fluid having contaminants therein. More specifically, the present invention relates to a hygrometer which is used in a textile processing environment where lint, fumes, condensable oils, tints and resins, or the like, are contaminants in the gaseous fluid being monitored, the hygrometer being capable of continuous use in this environment because a fresh or new wicking surface is always exposed to the gaseous fluid.

BACKGROUND OF THE INVENTION

Measurement and/or control of humidity and temperature of a gaseous fluid in a textile treating chamber, whether it is for drying or heat setting or other purposes, plays a vital role in assuring quality, maximum efficiency and productivity of the system. In the past, humidity measurement devices using various types of sensors failed to meet the tough requirements of a textile processing environment wherein the gaseous fluids contained lint, fumes, condensable oils, tints and resins, or the like, as these contaminants fouled the wick of the wet bulb sensing element after a period of use. In order to obviate the difficulty in utilizing simple humidity measuring devices which used a wet bulb sensor with a wick, highly-sophisticated systems were made available for use in the textile field, but these systems had the drawback that they required skilled technicians for operation and maintenance. Additionally, these highly-sophisticated systems had a high initial cost of installation.

PRIOR ART

Wet/dry bulb hygrometers have been heretofore used to monitor the relative humidity and temperature of a gaseous fluid with the relationship between the wet bulb and the dry bulb temperatures and the humidity being charted in the form of a psychrometric chart. However these prior art devices were not particularly effective in an environment where the gaseous fluid contained contaminants because the wick of the wet bulb sensor became fouled by contaminants in the gaseous fluids being monitored. The following patents represent prior art wet/dry bulb hygrometers or the like wherein the wick for the wet bulb sensor was fixed or stationary and thus did not present a fresh wicking surface during continuous monitoring:

U.S. Pat. No. 1,308,930 Carrier July 8, 1919
U.S. Pat. No. 1,601,243 Irwin, Jr. Sept. 28, 1926
U.S. Pat. No. 1,636,350 Armstromg July 19, 1927
U.S. Pat. No. 2,481,332 Newell, et al Sept. 6, 1949
U.S. Pat. No. 3,869,529, issued Mar. 4, 1975 to Donald T. Follett, discloses an air conditioning apparatus having a movable wick therein but this wick is utilized as a continuous liquid transporter belt to humidify air which has been filtered and heated prior to the air being returned to a room to ventilate the same.

BRIEF DESCRIPTION OF THE INVENTION

Briefly, the present invention relates to a wet/dry bulb hygrometer for monitoring and/or controlling humidity and temperature of a gaseous fluid having contaminants therein. The hygrometer includes a housing having an inlet and an outlet for the gaseous fluid and a passage extending therethrough from the inlet to the outlet. Blower means are provided in the passage for causing the gaseous fluids to be monitored to flow therethrough at a predetermined rate. A dry bulb sensor is provided in the passage for monitoring the dry bulb temperature, whereas a wet bulb sensor is also provided in the passage for monitoring the wet bulb temperature. The wet bulb sensor has a wick from a source of wick moving thereover so that a fresh wicking surface is exposed to the gaseous fluid. Means are provided for moving the wick material over the wet bulb sensor.

By moving the wick material over the wet bulb sensor, a new or fresh wicking surface is presented to the flow of gaseous fluid and, thus, contaminants cannot build up on the wick to an extent where the wet bulb sensor produces an inaccurate reading of wet bulb temperature. The hygrometer may be used in textile environment to continuously monitor and/or control the humidity and temperature of the gaseous fluid over long periods of time giving accurate results with a minimum of maintenance. Consequently, quality and uniformity of the textile finished goods can be upgraded as the chemical reaction and rate of reaction of the treating fluids are accurately controlled. Additionally, the textile apparatus, for example, a textile oven, can be operated at maximum capacity and at increased production speeds as the use of the hygrometer in monitoring and/or controlling the humidity and temperature results in substantial energy saving due to reduction in higher exhausts from such ovens.

Another aspect of the present invention is to provide a supply wick material stored on a spool immersed in a reservoir, the wick material being fed from the reservoir into the gaseous fluid passage of the hygrometer about the wet bulb sensor and then removed from the passage on a take-up spool. The wick material is positively pulled from the wet bulb sensor at a predetermined speed.

Still another aspect of the present invention is to make the wick material tubular in form and to feed the same onto the free end of the wet bulb sensor, the wick material being slit as it is removed from the wet bulb sensor.

A further aspect of the present invention is to utilize a wick material made in the form of a flat ribbon, the wick material passing into the hygrometer and being shaped around the wet bulb sensor by suitable forming means with further means being provided to maintain the flat ribbon wick around the wet bulb sensor while in the passage of the hygrometer.

Another aspect of the present invention is to provide a hygrometer with a housing having a first portion mounted exteriorly of a textile treating chamber and a second portion extending through the wall of the treating chamber and having an inlet and an outlet for the flow of gaseous fluid through a passage extending from the inlet to the outlet through the first portion of the housing.

These and other features and advantages of the present invention will appear more fully in the following Detailed Description of the Invention when taken with reference to the accompanying drawings.

BRIEF DESCRIPTION OF THE DRAWINGS

FIG. 1 is a top plan view of the present invention partly in elevation and partly in section and illustrating the hygrometer installed on a wall of a textile treating apparatus such as an oven;

FIG. 2 is an enlarged vertical view looking in the direction of the arrow A in FIG. 1 of the hygrometer of the present invention with a side cover plate of the housing removed;

FIG. 3 is an enlarged fragmentary perspective view of the drive rolls for removing the wick and the knife means for slitting the tubular wick;

FIG. 4 is a fragmentary top view partly in section and illustrating the drive for the wick take-up spool, the upper drive roll being omitted for purpose of clarity;

FIG. 5 is a fragmentary view looking in the direction of the arrow B in FIG. 4, the spring for the torque arm being omitted;

DETAILED DESCRIPTION OF THE DRAWINGS

Figure 6:
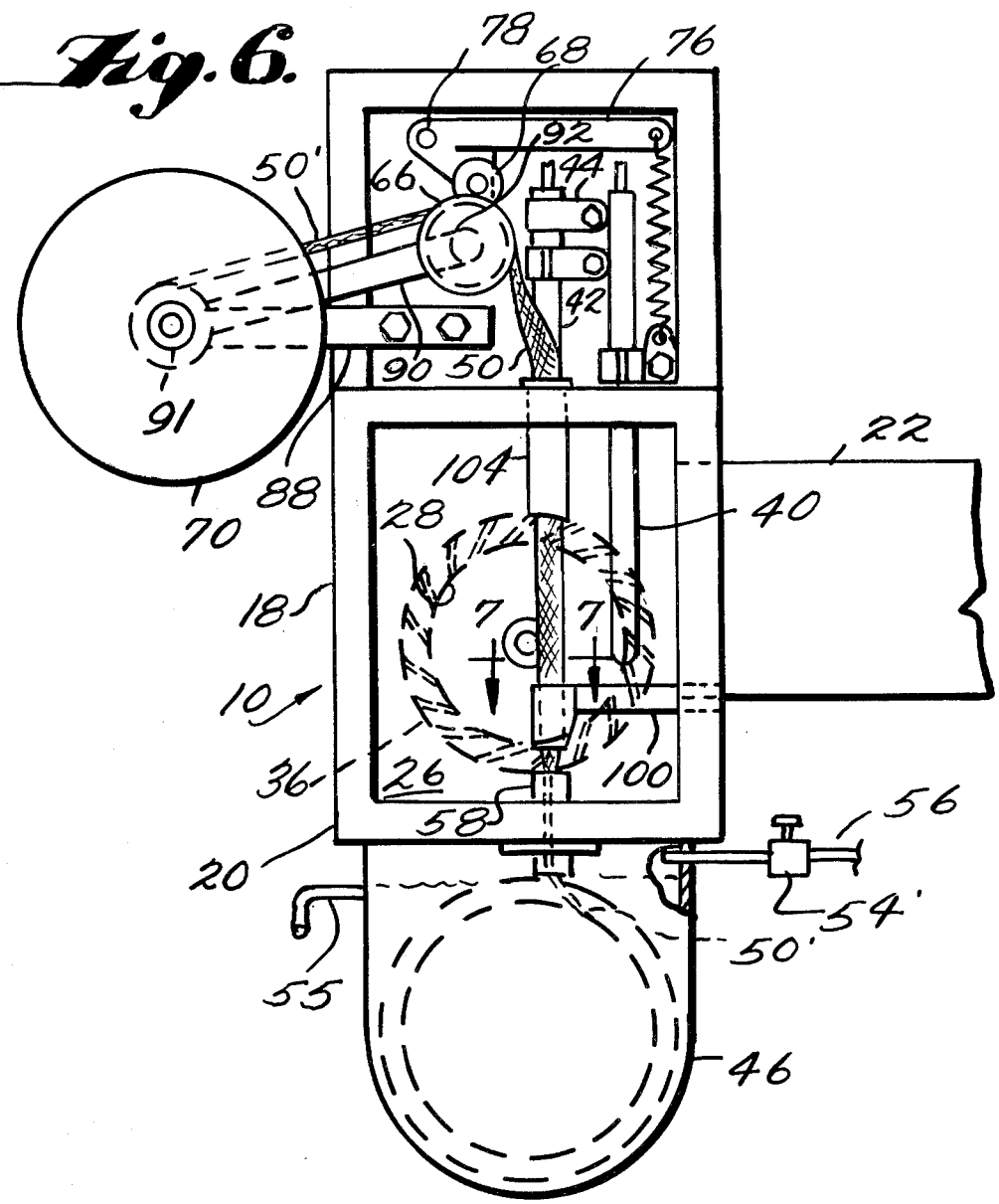
FIG. 6 is a view similar to FIG. 2 but showing a modified arrangement for feeding a flat ribbon wick about the wet bulb sensor.

Referring now to the drawings wherein like characters or reference numerals represent like or similar parts, the wet/dry bulb hygrometer of the present invention is generally illustrated in FIGS. 1 through 5. In more detail, the wet/dry bulb hygrometer, generally designated at 10, is mounted on a textile treating apparatus, generally designated at 12, the textile treating apparatus 12 being illustrated as an oven having a treating chamber 14 defined by a housing 16. The wet/dry bulb hygrometer 10, which is of the psychrometer type, is utilized for monitoring and/or controlling the humidity and temperature in the chamber 14 by sensing the wet bulb temperature and dry bulb temperature, the relationship of these temperatures being charted in the form of a psychrometric chart. While the hygrometer 10 is illustrated as just monitoring the wet and dry bulb temperatures of the chamber 14, the signals sensed may be used with electronic hardware or a microprocessor control system to operate dampers or the like on the oven 12 to control the humidity and temperature within the chamber 14. By controlling the humidity within the chamber 14 to an optimum value, there can be substantial energy savings in the operation of the oven. This permits the oven to be operated at maximum efficiency at all times and, in effect, increases production speeds.

The gaseous fluid within the oven used for treating textile material may be steam, dry air, or the like, but it will be appreciated by those skilled in the art that such gaseous fluid can pick up contaminants from the textile material being treated, such as lint, fumes, condensable oils, tints and resins. These contaminants in the gaseous fluid will in a short period of time foul up the wick of a wet bulb sensor thus causing such a sensor to give an inaccurate reading of set bulb temperature. The present invention obviates such a disadvantage of prior hygrometers when used to monitor the wet bulb temperature of gaseous fluid having contaminants therein as the wicking surface exposed to the gaseous fluid is changed either continuously or intermittently so that there can not be a buildup of contaminants which would affect the wet bulb temperature sensed.

The hygrometer 10 of the present invention includes a housing 18 which has a first portion 20 mounted exteriorly of the oven 12 and a second portion 22 projecting through an opening 24 in the wall 16 of the oven 12 into the chamber 14. The housing 18 is provided with a vertical partition wall 26 that extends through the first portion 20 and second portion 22. Partition wall 26 in the first portion 20 is provided with an opening 28 therein and, thus, a passage 30 extends through the housing 18. As shown in FIG. 1, the housing 18 is provided on its second portion 22 with an opening 32 that defines an inlet for the passage 30 and a second opening 34 which defines an outlet for the passage 30. The gaseous fluid from the oven 12 enters the inlet 32 and flows though the passage 30, as shown by the arrows in FIG. 1, and then flows through the opening 28 and out of the outlet 34 back into oven 12. In order to cause the flow of gaseous fluid through the passage 30 at a predetermined velocity, the housing 18 is provided with a centrifugal fan-type blower 36 driven by an electric motor 38. It has been found that the velocity of the gaseous fluid should be in excess of 4 meters per second when it passes over the sensors.

The hygrometer 10 is provided with a dry bulb thermometer or sensor 40 which extends through the housing 18 into the passage 30 and a wet bulb thermometer or sensor 42 which also extends through the housing 18 into the passage 30. Preferably, the wet bulb sensor 42 and dry bulb sensor 40 are positioned in the passage 30 upstream of the blower 36 and they may be supported exteriorly of the housing 18 by means of brackets 44 secured to superstructure 64 on the top of housing 18.

Supported beneath the housing 18 is a reservoir 46 for water, the reservoir 46 rotatably supporting a supply spool 48 for wick material 50 which is to pass over the wet bulb sensor 42. The water level in the reservoir 46 is controlled by a float 52 which in turn operates a needle valve 54 in the water inlet line 56. Alternatively, as shown in FIG. 6, just a needle valve 54' may be used to continuously supply water, the level being maintained by an overflow pipe 55.

A thimble or tubular sleeve 58 is provided in the bottom of the housing 18 and acts as an inlet for the wick material 50 to the passage 30 of housing 18. As shown in FIGS. 2 and 3, the wick material 50 is tubular and is porous and it slips over the free end of the web bulb sensor 42, and in order that it can be removed from the upper attached end of the wet bulb sensor 42, a knife 60 carried by a bracket 62 is supported on superstructure 64 above the housing 18. The knife 60 is positioned closely adjacent to the wet bulb sensor 42 on the end portion of the same which extends out of the housing 18 and it slits the tubular wick material 50 as the wick material is being pulled.

As explained earlier in the specification, it is necessary to always present a fresh wicking surface of wick material to the stream of gaseous fluid flowing over the same so as to avoid the wick material from being fouled up by contaminants in the gaseous fluid and, thus, providing an inaccurate signal for the wet bulb temperature. In order to accomplish the movements of the wick material 50 over the wet bulb sensor 42, a pair of positively driven drive rolls 66 and 68 pull the wick material 50 upwardly over the wet bulb sensor 42 and cause the knife 60 to slit the same, the used wick material 50 being taken up on a driven take-up spool 70. The lower drive roll 66 is carried on a drive shaft 72 of a high reduction synchronous gear motor 74 suitably supported on the superstructure 64. The high reduction synchronous gear motor 74 is a Trogetec Model GS-1 made by Trochoidal Gear Technology, Inc., Ithaca, N.Y., or some other suitable motor geared down to a slow and steady drive. Preferably, the motor 74 continuously operates to cause continuous movement of the wick material 50, although it could possibly operate intermittently. In any event, the operation of the motor is such that the wick material 50 is moved very slowly in the order to 5–10 centimeters per day. In other words, by moving the wick material 50 across the wet bulb sensor 42 at a velocity of at least 5–10 centimeters per day, the wick material 50 will not be fouled by contaminants to the extent where inaccurate wet bulb temperatures are sensed. Since the supply spool 48 holds 15 meters of wick material 50, it will be appreciated that the hygrometer 10 can monitor and/or control the humidity and temperature of the textile treating apparatus 12 continuously for about 150–300 days.

Referring to FIGS. 2 through 5, inclusive, it will be noted that the upper drive roll 68 is rotatably carried on one end of an L-shaped torque arm 76, the torque arm 76 being pivotally mounted on the superstructure 64 on the housing at 78. A spring 80 extending from the other or free end of the torque arm 76 is connected to the bracket 44 supporting the dry bulb sensor 40 and this urges the torque arm 76 in a clockwise direction as viewed in FIG. 2 and thus causes the drive roll 68 to be spring urged toward the drive roll 66 with the wick material 50 interposed therebetween. Drive rolls 66 and 68 are provided with gears 82 and 84, respectively, the gears meshing and, therefore, the upper drive roll 68 is also positively driven. As shown in FIG. 5, the lower drive roll 66 may be provided with the cap plates 86 which help to hold in line the wick material 50 being removed from the wet bulb sensor 42. Lower drive roll 66, or drive roll 68 also, if desired, preferably is knurled to provide more positive pull on the wick material.

Figure 9:
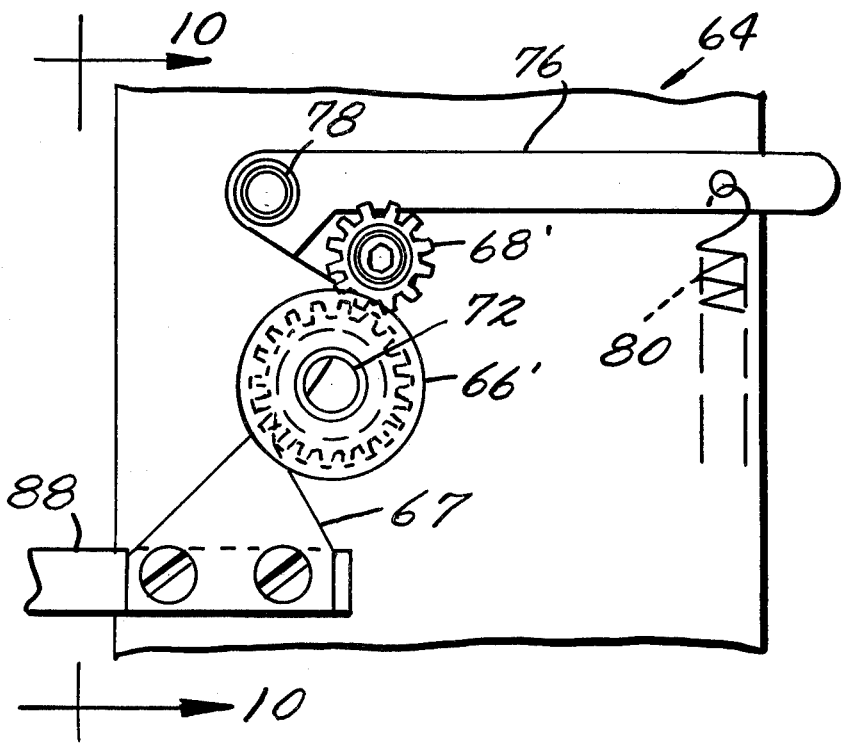
FIG. 9 is an enlarged fragmentary vertical view similar to FIGS. 2 and 6 but illustrating a modified embodiment of meshing gears for moving the spent wick off of the wet bulb sensor.
Figure 10:
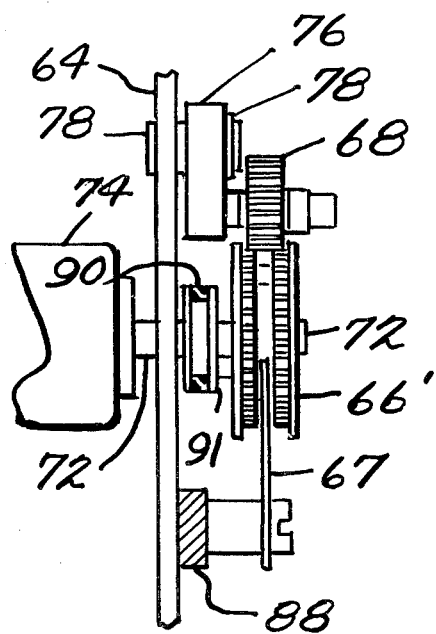
FIG. 10 is a sectional view taken on the line 10—10 of FIG. 9.

Referring to FIGS. 9 and 10, still more preferred as an embodiment of drive rolls 66 and 68 is for the rolls themselves to be in the form of meshing gears, 66' and 68', thus dispensing with gears 82 and 84. Since the spent wick in this embodiment actually passes through the meshing teeth of gears 66' and 68', minimal potential for wick slippage and maximum control of drive are achieved. In this embodiment a tendency for the wick to stick to the lower gear 66', thereby even lapping it, is overcome by provision of an optional delta-shaped guide member 67, attached by the mounting screws of bracket 88 so that the upper point of the delta-shaped guide member 67 contacts gear 66' at about its 8 o'clock position, to insure breakaway of the wick from the gear teeth. Said delta-shaped member 67 is conveniently made from sheet metal or similar material.

As best shown in FIG. 4, the take-up spool 70 for the spent or used wick material 50 is suitably carried on a bracket 88 mounted on the superstructure 64 of the housing 18. In order that it may be positively driven in timed relationship to movement of the drive rolls 66 and 68, an endless belt drive 90 is provided, the belt drive 90 extending about a pulley 91 keyed to the drive shaft 72 of motor 74 and about pulley 92 keyed to the take-up spool shaft 94.

Figure 7:
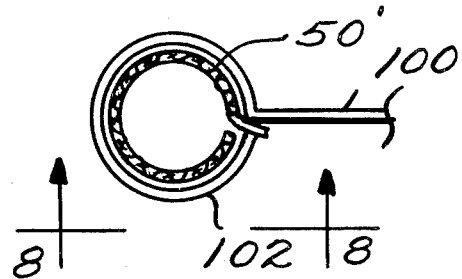
FIG. 7 is an enlarged sectional view taken on the line 7—7 of FIG. 6 and illustrating the forming means for wrapping the flat ribbon wick about the wet bulb sensor.
Figure 8:
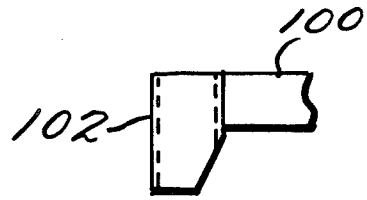
FIG. 8 is a view on reduced scale taken on the line 8—8 in FIG. 7.

Referring to FIGS. 6 through 8 of the present invention, there is disclosed a modification for the hygrometer 10 when the wick material 50 is a flat ribbon 50' rather than tubular. In this modification of the invention, a forming or shaping member 100 is provided for forming the flat ribbon 50' around the wet bulb sensor 42. The forming member 100 is an element mounted within the housing 18 in the passage 30 and it has an open looped end 102 which is axially aligned with the wet bulb sensor 42. The diameter of the open looped end 102 is slightly greater than the diameter of the wet bulb sensor 42 and it causes the flat ribbon wick 50' to be rolled around the web bulb sensor 42. The upper portion of the housing 18 is provided with a sleeve 104 and this sleeve 104 maintains the wick material 50' around the wet bulb sensor 42 while the wick material 50' is in the passage 30 and until the flat ribbon wick 50' passes out of the housing 18 and is again flattened when the drive rolls 66 and 68 pull the flat ribbon wick 50' upwardly through the housing 18.

When the textile treating apparatus 12 is an oven, its temperature may be typically set at 350°–400° F., and as mentioned previously, the gaseous fluid must flow from the oven through the hygrometer and return to the oven at a velocity in excess of 4 meters per second in order to obtain accurate monitoring of the humidity and temperature of the gaseous fluid therein. At this velocity, it is found that the wick of the wet bulb sensor must be moved at least 5–10 centimeters per day in order to avoid fouling of the same by contaminants in the gaseous fluid. Consequently, the motor 74 can either be driven continuously very slowly to cause such movement or the motor 74 can be intermittently operated by a timer but still slow enough not to cause damage to the wick when the wick is pulled.

Although the present invention has been described in connection with the textile treating apparatus such as an oven, it will be appreciated by those skilled in the art that the hygrometer of the present invention may be used in any situation where it is necessary to monitor for long periods of time the humidity and temperature of gaseous fluids having contaminants therein.

The terminology used throughout this specification is for the purpose of description and not limitation, the scope of the invention being defined in the appended claims.

What is claimed is:

1. A wet/dry bulb hygrometer for monitoring and/or controlling humidity and temperature of a gaseous fluid having contaminants therein, said hygrometer comprising:
   a housing having an inlet and an outlet for a gaseous fluid and a passage extending therethrough from the inlet to the outlet;
   blower means in said passage for causing the flow of gaseous fluid therethrough at a predetermined rate of flow;
   a dry bulb sensor extending into said passage;
   a wet bulb sensor extending into said passage;
   a source of wick material for said wet bulb sensor;
   means for moving said wick material over said wet bulb sensor to provide a fresh wicking surface therefor; and
   means to wet said wick material.

2. A wet/dry bulb hygrometer as claimed in claim 1 including a storage spool for said wick material, and in which said means to wet said wick material includes a reservoir for water, said spool of wick material being mounted in said reservoir.

3. A wet/dry bulb hygrometer as claimed in claim 2 in which said means for moving said wick material over said wet bulb sensor includes a pair of drive rolls spring urged toward each other and through which said wick material passes, a take-up spool to receive the wick material from said drive rolls and motor means for positively driving said pair of drive rolls and said take-up spool at a predetermined speed.

4. A wet/dry bulb hygrometer as claimed in claim 3 in which one of said drive rolls is carried on a torque arm pivotally mounted to said housing, and the other of said drive rolls is directly connected to said motor means, said drive rolls having mating gears.

5. A wet/dry bulb hygrometer is claimed in claim 3 in which said wick material is tubular and passes over said wet bulb sensor and in which knife means are provided for cutting said tubular wick material whereby it may be removed from said wet bulb sensor by said pair of drive rolls.

6. A wet/dry bulb hygrometer as claimed in claim 5 in which said knife means includes a blade operatively supported from said housing and positioned adjacent said web bulb sensor.

7. A wet/dry bulb hygrometer as claimed in claim 3 in which said wick material is in flat ribbon form and including means carried by said housing for forming said flat ribbon wick around said web bulb sensor.

8. A wet/dry bulb hygrometer as claimed in claim 7 in which said forming means includes a member having an open looped shaped element axially aligned with said wet bulb sensor and through which said flat ribbon wick passes and is shaped about said wet bulb sensor.

9. A wet/dry bulb hygrometer as claimed in claim 8 including a sleeve member through which said wet bulb sensor extends, said sleeve member maintaining said flat ribbon wick around said wet bulb sensor as it passes through said passage.

10. A wet/dry bulb hygrometer as claimed in claim 3 in which said motor means is a high-reduction synchronous gear motor for moving said wick material on said wet bulb sensor at a velocity in the order of 5 to 10 centimeters per day.

11. A wet/dry bulb hygrometer as claimed in claim 10 in which said motor is continuously operated.

12. A wet/dry bulb hygrometer as claimed in claim 10 in which said motor is intermittently operated.

13. A wet/dry bulb hygrometer as claimed in claim 10 in which said blower means causes said gaseous fluid to flow across said wet bulb sensor and said dry bulb sensor at a velocity in excess of 4 meters per second.

14. A wet/dry bulb hygrometer as claimed in claim 3 in which said drive rolls are gears having meshing teeth through which said wick material passes, one of said drive rolls being directly connected to and driven by said motor means and the other of said drive rolls being carried on a torque arm pivotally mounted to said housing.

15. In combination:
an apparatus for treating materials with a gaseous fluid, said apparatus having a housing defining chamber for the materials; and
a wet/dry bulb hygrometer for monitoring the humidity and temperature of the gaseous fluid within the chamber, said hygrometer including a housing having a first portion mounted exteriorly of the chamber and having a second portion extending through a wall of the chamber, said hygrometer housing having a passage therethrough extending from an inlet in said second portion positioned within the chamber of said apparatus housing to an outlet in said second portion positioned within the chamber of said apparatus housing, a blower means in said passage in the first portion of said hygrometer housing for causing flow of gaseous fluid therethrough at a predetermined rate of flow, a dry bulb sensor extending through said first portion of said hygrometer housing into said passage, a rod-like wet bulb sensor extending through said first portion of said hygrometer housing into and having a free end in said passage, a source of wick material exterior of said hygrometer housing for said wet bulb sensor, means for moving said wick material through said first portion of said hygrometer housing into said passage and over said wet bulb sensor and then out of said first portion of said hygrometer housing whereby a fresh wicking surface is provided for said wet bulb sensor, and means exterior of said hygrometer housing for wetting said wick material.

16. The combination as claimed in claim 15 in which said means to wet said wick material includes a reservoir for water and in which said source of wick material includes a spool mounted in said reservoir.

17. The combination as claimed in claim 16 in which said means for moving said wick material over said wet bulb sensor includes a pair of drive rolls spring urged toward each other and through which said wick material passes after leaving said wet bulb sensor, a take-up spool to receive the wick material from said drive rolls, and motor means for positively driving said pair of drive rolls and said take-up spool at a predetermined speed.

18. The combination as claimed in claim 17 in which said wick material is in flat ribbon form and including means carried by said housing for forming said flat ribbon wick around said wet bulb sensor.

19. A wet/dry bulb hygrometer as claimed in claim 17 in which said drive rolls are gears having meshing teeth and through which said material passes, one of said drive rolls being directly connected to and driven by said motor means and the other of said drive rolls being carried on a torque arm pivotally mounted to said housing.

20. The combination as claimed in claim 16 in which said wick material is tubular and passes over the free end of said wet bulb sensor and in which knife means are provided for cutting said tubular wick material whereby it may be removed from said wet bulb sensor by said pair of drive rolls.

21. The combination of claim 15 in which said wick moving means moves the wick over said wet bulb sensor at a velocity in the order of 5 to 10 centimeters per day.

22. The combination as claimed in claim 21 in which said blower means causes gaseous fluid to flow across said wet bulb sensor at a velocity in excess of 4 meters per second.

23. The combination as claimed in claim 15 in which said textile apparatus is an oven and in which said oven has a temperature in a range of 350°–400° F.

24. The combination of claim 23 in which said oven humidity is generally in an area of 0.01 to 0.2 pound of water per pound of dry air.

* * * * *

UNITED STATES PATENT AND TRADEMARK OFFICE
CERTIFICATE OF CORRECTION

PATENT NO. : 4,175,436

DATED : November 26, 1979

INVENTOR(S) : CRAWFORD et al

It is certified that error appears in the above-identified patent and that said Letters Patent is hereby corrected as shown below:

Column 2,
line 19, after "in" and before "textile" insert the article --a--

Column 7,
claim 5, line 17, after "hygrometer" and before "claimed" delete the word "is" and insert --as--.

Signed and Sealed this

Twentieth Day of November 1984

[SEAL]

Attest:

GERALD J. MOSSINGHOFF

Attesting Officer     Commissioner of Patents and Trademarks